(12) United States Patent
Ting et al.

(10) Patent No.: US 6,443,906 B1
(45) Date of Patent: Sep. 3, 2002

(54) METHOD AND DEVICE FOR MONITORING BLOOD PRESSURE

(75) Inventors: Choon Meng Ting; Ngak Hwee Chua, both of Singapore (SG)

(73) Assignee: Healthstats International PTE Ltd., New Park Centra Shopping Arcade (SG)

( * ) Notice: Subject to any disclaimer, the term of this patent is extended or adjusted under 35 U.S.C. 154(b) by 0 days.

(21) Appl. No.: 09/694,847

(22) Filed: Oct. 20, 2000

(30) Foreign Application Priority Data

Oct. 9, 2000 (SG) .................................... 200005776-0

(51) Int. Cl.[7] .............................................. A61B 5/02
(52) U.S. Cl. ...................... 600/490; 600/485; 600/503
(58) Field of Search ............................ 600/485, 490, 600/503

(56) References Cited

U.S. PATENT DOCUMENTS

| | | | | |
|---|---|---|---|---|
| 4,307,727 A | * | 12/1981 | Haynes ........................ | 600/485 |
| 4,331,154 A | * | 5/1982 | Broadwater et al. ......... | 600/490 |
| 5,309,916 A | * | 5/1994 | Hatschek ................ | 600/485 Q |
| 5,406,952 A | * | 4/1995 | Barnes et al. ................ | 600/485 |
| 5,485,848 A | * | 1/1996 | Jackson et al. ............. | 600/485 |
| 5,568,814 A | | 10/1996 | Gallant et al. | |
| 6,290,650 B1 | * | 9/2001 | Butterfield et al. ......... | 600/485 |

FOREIGN PATENT DOCUMENTS

| | | |
|---|---|---|
| EP | 0297224 | 1/1989 |
| JP | 5329117 | 12/1993 |

OTHER PUBLICATIONS

Patent Abstracts of Japan of JP05329117 dated Dec. 14, 1993.

* cited by examiner

*Primary Examiner*—Kevin Shaver
*Assistant Examiner*—Patricia C. Mallari
(74) *Attorney, Agent, or Firm*—Ladas & Parry

(57) ABSTRACT

A device for continuously monitoring a user's arterial blood pressure has a sensor adapted to continuously detect the blood pressure and to generate signals representative thereof by contact with an external surface of the user's body at a location adjacent an artery. The sensor is securely held in operable contact with the user's body at the location. A microprocessor interprets the signals generated by the sensor to determine actual arterial blood pressure. The sensor includes a projecting portion for detecting and transmitting changes in blood pressure, wherein the projecting portion is adapted to effect at least partial occlusion of the artery at the location.

24 Claims, 14 Drawing Sheets

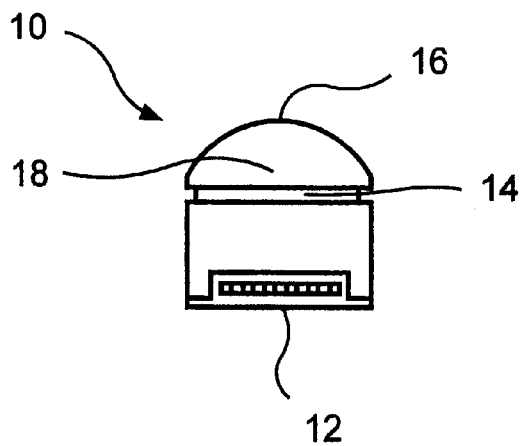
F I G. 2

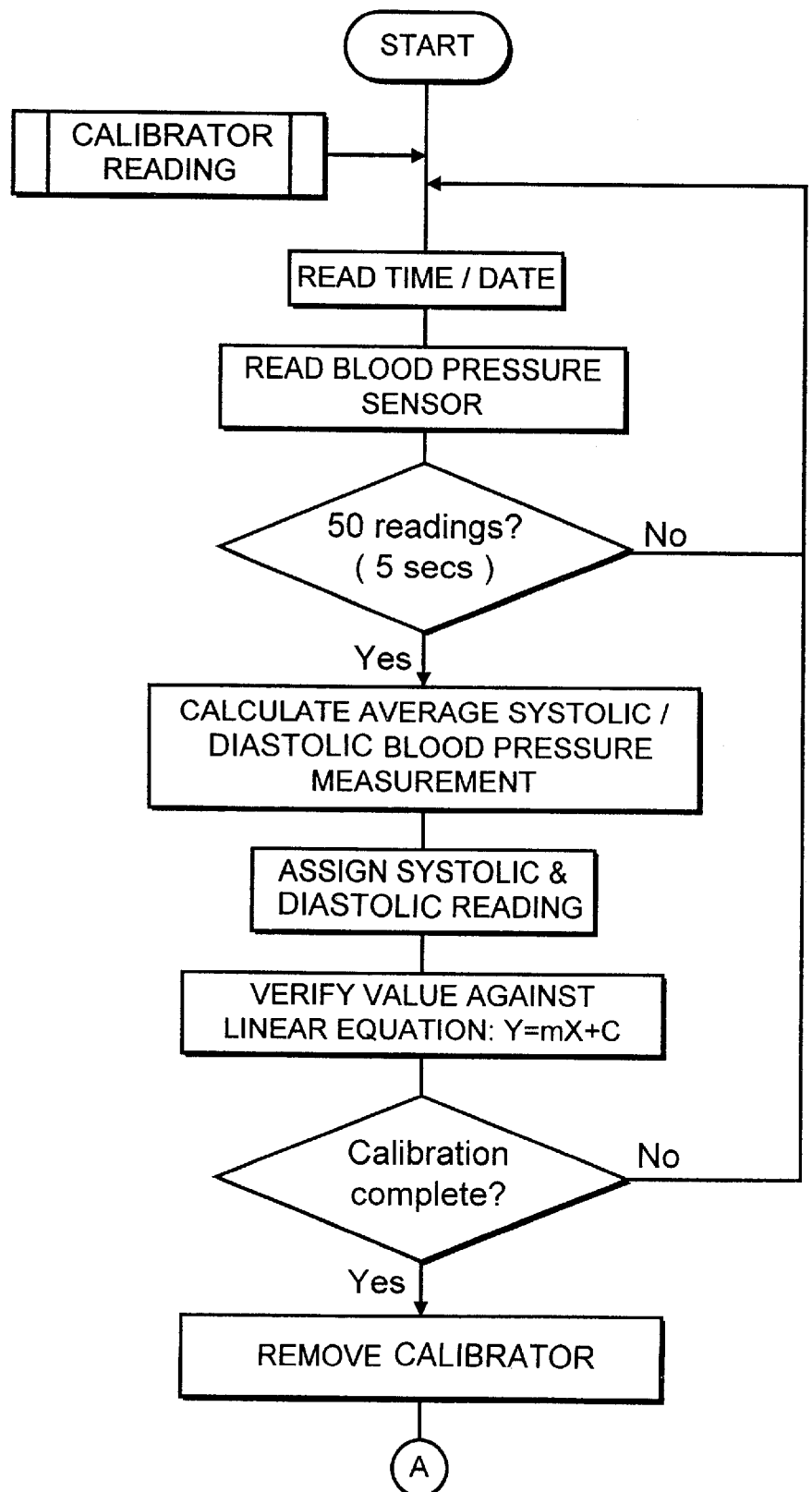
F I G. 14

METHOD AND DEVICE FOR MONITORING BLOOD PRESSURE

FIELD OF THE INVENTION

The present invention relates to a method and device for monitoring blood pressure. In particular, such method and device is non-invasive to the human body and the device is preferably portable.

BACKGROUND AND PRIOR ART

In Singapore alone, there is at least one person coming down with stroke every hour. The numbers are rising year after year. Moreover, death from stroke in Singapore accounts for more than 12% of all deaths since 1996. Together with heart ailment, it accounts for more than 32% of all deaths since 1996, ie. more than one-third of all mortalities in Singapore.

Further, every year there are about 27,000 to 30,000 pregnancies leading to successful deliveries. Of these, thousands of pregnant women suffer from a condition called pre-eclampsia. This is a condition whereby the mother suffers from a rise in blood pressure during pregnancy. The blood pressure can rise to dangerous levels without warning and it can lead to convulsion and brain damage to the mother, and sudden intra-uterine death of the baby. The morbidity and mortality of pre-eclampsia is directly related to the level and control of blood pressure of the patient.

The central event linking the 3 major ailments is blood pressure. In fact, in many instances of strokes and heart attacks, the usual and final pathway is a sudden and dangerous rise in blood pressure before catastrophe strikes. Therefore, the detection and prevention of further rises or falls in the final pathway holds the key to the prevention and reduction of strokes, heart attacks and eclampsia.

Currently, patients who suffer from the above illnesses are monitored either as outpatients or in-patients in a hospital. The majority of these are outpatients. When one visits a doctor, be it monthly or fortnightly, the blood pressure reading is obtained by using a blood pressure cuff sphygmomanometer. They use occlusive methods, i.e. air is pumped into the cuff to occlude the artery and is slowly released to finally allow the blood to overcome the resistance and flow through. A flow turbulence is thus set up and picked up by the doctor listening to it. The blood pressure is then recorded. The self-monitoring devices that are available on the market generally all use occlusive methods, the difference being the turbulence are picked up by various methods, such as via a microphone. In other words, the number of readings is totally dependent on the number of times that the artery is being occluded, whether it is manual or pre-set electronically. The monitoring is therefore not continuous, in the sense of having beat-to-beat readings.

To make matters worse, whenever the doctor detects a normal or "good" blood pressure in his clinic, he usually makes 3 assumptions:
1. the patient's blood pressure from the last test must be "good";
2. his blood pressure until the next test will be "good";
3. therefore, he will not have a stroke, heart attack or convulsion as in the case of a pre-eclampsic woman.

Unfortunately, these assumptions are far from the truth as the above incidents have revealed. Therefore, it would be advantageous to be able to catch the "final pathway" of sudden changes in blood pressure/pulse, by being able to monitor a person's blood pressure continuously and be able to sound the alarm at the right time to prevent a catastrophe.

One method of continuously monitoring blood pressure is suggested in U.S. Pat. No. 5,485,848. That patent purports to disclose a non-invasive and non-intrusive portable device for monitoring a user's arterial blood pressure. However, that device has the disadvantage that it needs to fix a nominal or base pressure by fixing the strap tension. The calibration is also user-specific. It assumes that base pressure can be maintained constant for the calibration to work. It is not practically possible to fix the base pressure of a moving wrist by the methods described. At most, it only keeps the strap circumference constant, instead of keeping the pressure constant. By fixing the circumference of the strap, pressure changes are even greater with movement and changes in position of the hand. Thus, the wrist position cannot change. In practice, it is difficult to keep the pressure constant as a slight change in wrist pressure and sensor position affects readings to an appreciable extent. Furthermore, the calibration involves extrapolation and interpolation of readings. Therefore, user conditions must remain uniform, since one has to show a linear relationship which may not exist if user conditions are otherwise. In accordance with the described formula for calculating blood pressure, the pressure sensed by the piezo-electric film transducer is dependent on the area of contact, distance from the artery and source of the signal. These are factors which cannot practically be fixed with the described device.

To provide continuity in monitoring, the blood pressure must be measured on a beat-to-beat basis, as in intra-arterial monitoring.

The time-keeping function of a watch should be integrated with the blood pressure data, as this will provide a meaningful interpretation of the trend or pattern of blood pressure seen or recorded over a period of time. The downloading of data over time may become important in an unfortunate event of the death of a wearer.

Similarly, in the collection of data by the sensor, the position of the sensor and the fixation of the sensor must be considered. In order to accurately collect data from every beat of the heart, the sensor compartment must be able to receive reliable data with the wrist in different positions. In the prior art, the data can only be reliably collected when the hand is held fixed at a certain position, i.e. with restrictions. The prior art may try to overcome the movement of the strap by increasing the strap pressure. Usually, this is not only impractical, but undesirable as the compression of veins will cause significant congestion in the hand distal to it in just a few minutes. This can lead to numbness and further medical complications.

The Median Nerve at the Carpal Tunnel would be compressed causing numbness of the finger in a few minutes. As a result, the hand or fingers will swell, causing further congestion. This not only greatly affects the signal, but is harmful to the wearer. Therefore, the challenge is to be able to design the strap system that is comfortable to the wearer over a long period and holds the sensor in position well so as to allow for natural movement of the hand/wrist and collects the data accurately.

The donning and doffing of the wrist monitor and the whole calibration has to be simple and user-friendly for it to be of value for a person who is not medically trained.

Against this medical background and clinical deficiency, the problem is to provide an improved device and method for continuous and non-invasive monitoring of arterial blood pressure. Such a device should preferably be capable of alarming the user of harmful rises or falls in the user's blood pressure.

SUMMARY OF THE INVENTION

According to one aspect of the present invention, there is provided a device for continuously monitoring a user's arterial blood pressure, including:

sensor means adapted to continuously detect said blood pressure and to generate signals representative thereof by contact with an external surface of the user's body at a location adjacent an artery;

attachment means for securely holding the sensor means in operable contact with the user's body at the said location; and microprocessor means for interpreting said signals generated by the sensor means to determine actual arterial blood pressure;

wherein the sensor means includes a projecting portion for detecting and transmitting changes in blood pressure, and wherein the projecting portion is adapted to effect at least partial occlusion of the artery at the said location.

In a preferred embodiment of the invention the attachment means is adapted to non-penetratingly press the projecting portion into the surface of the user's body for operable contact therewith at said location adjacent the artery.

In a preferred embodiment of the invention the senor means includes a transducer and the projecting portion of the sensor means is adapted to transmit detected changes in blood pressure to the transducer. Preferably, the projecting portion of the sensor means is a dome-shaped plunger connected to the transducer.

According to another aspect of the present invention, there is provided a method for continuously monitoring a user's arterial blood pressure, including the steps of:

providing sensor means adapted to continuously detect said blood pressure and to generate signals representative thereof by contact with an external surface of the user's body at a location adjacent an artery;

maintaining the sensor means in operable contact with the user's body such that said sensor means effects at least partial occlusion of the artery at the said location; and computing the actual arterial blood pressure detected by the sensor means using microprocessor means adapted to interpret the signals generated by the sensor means.

In a preferred embodiment of the invention the step of maintaining the sensor means in operable contact with the user's body includes the step of non-penetratingly pressing a projecting portion of the sensor means into the surface of the user's body.

In a preferred embodiment of the invention the step of maintaining the sensor means in operable contact with the user's body includes the step of securely holding the sensor means at the said location by attachment means such as a strap.

In developing a blood pressure monitoring device according to a most preferred embodiment of this invention, there are various design considerations which should be met. A truly effective device for continuous blood pressure monitoring should meet the following basic requirements:

1. Portability.
2. Continuity.
3. Accuracy in the calibration, collection of data and ability to function in a natural environment without interruption to daily activities.
4. User-friendly so that there is no need for medically-trained personnel to operate the device.
5. It must not cause any other medical complications
6. It should advantageously be useable also as a communications tool in order to manage the data collected.

It will be convenient to hereinafter describe the invention in greater detail by reference to the accompanying drawings which illustrate one particularly preferred embodiment. The particularity of the drawings and the related description is not to be understood as superseding the generality of the broad identification of the invention.

BRIEF DESCRIPTION OF THE DRAWINGS

The drawings relate to one preferred embodiment of the invention.

FIG. 2 is a side view of a sensor according to the preferred embodiment of the invention.

FIG. 14 is a flow-chart summarizing the steps involved in the calibration procedure.

DETAILED DESCRIPTION OF A PREFERRED EMBODIMENT OF THE INVENTION

According to the preferred embodiment of the present invention, there are several major components in the design of the device. They are the sensor system to measure the blood pressure, the strap system to secure the sensor relative to an artery and the watch head for calibration and other interfacing purposes.

Measuring of Blood Pressure

The principle behind the design of the present invention is to mimic the intra-arterial measurement of blood pressure. This intra-arterial method of blood pressure measurement is at present invasive to the human body.

Figure 1:
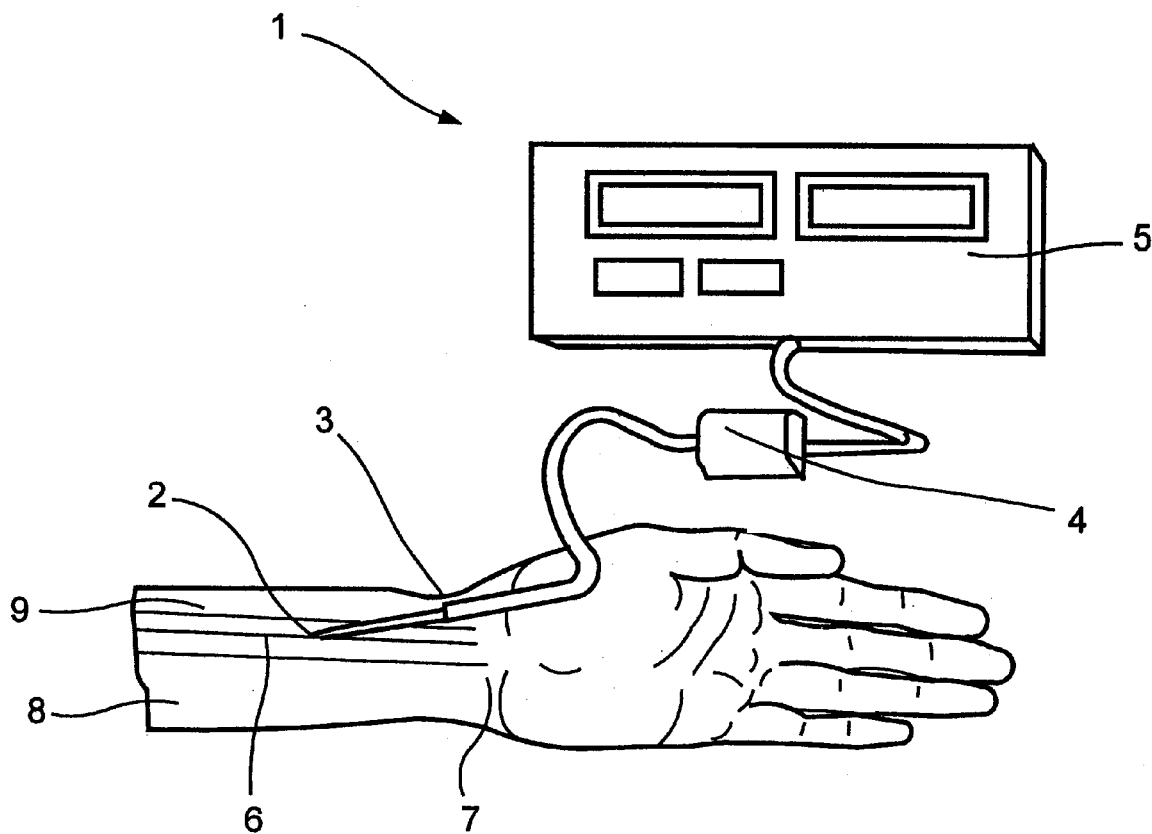
FIG. 1 is an illustration of an intra-arterial blood pressure monitoring device of the prior art.

FIG. 1 is an illustration of an intra-arterial blood pressure monitoring device 1 of the prior art. The intra-arterial blood pressure monitoring device 1 generally comprises an intra-arterial cannula 2, that is inserted into the radial artery 6 of a patient's wrist 7. As is apparent from FIG. 1, the radial artery 6 is adjacent the radial bone 8. The intra-arterial cannula 2 is connected to a fluid interface 3, containing a fluid column. The fluid interface 3 is connected by a tube to a microprocessor and sensor unit 4. The microprocessor and sensor unit 4 detects changes in the blood pressure in the radial artery 6 and this information is transmitted to a pressure display unit 5.

In the intra-arterial blood pressure measuring device 1 the blood pressure in the radial artery 6 is sensed, beat-to-beat by the blood column in the inducting cannula 2. The beat-to-beat changes acts on the column of fluid, which is incompressible and will faithfully relay the pressure change to the microprocessor. The electronic change in signal is then converted to a digital form and displayed on a graph on the display 5, the systolic being the pressure value when the heart pumps, and diastolic, the pressure of the column at rest.

The primary disadvantage of the intra-arterial blood pressure monitoring device 1 is that it is invasive. The patient feels discomfort and pain as the intra-arterial cannula 2 is inserted into his skin 9 and artery 6. Furthermore, the device 1 is also not portable, such that it is normally only used in a hospital environment. It is not possible to monitor a person's blood pressure continuously when he is going about his normal daily activities. Intra-arterial measurements cannot be taken with any movement of the wrist. Therefore, the whole wrist must be immobilised, as during an operation.

In the design of the present invention, the whole system including the strap, the sensor and the wrist head have to be considered together in order to appreciate the similarity in principle to the intra-arterial cannula 2.

Components of the Sensor System

FIG. 2 is a side view of a sensor 10 according to the preferred embodiment of the invention. The sensor 10 includes a transducer 12 which produces a voltage output according to pressure changes acting on its diaphragm 14. A plunger 16 is affixed next to the diaphragm 14 of the transducer 12.

The plunger 16 is a specially designed hemispherical component made of metal. It sits on the diaphragm 14 of the transducer 12, preferably covering substantially the base of the transducer 12. The purpose of the diaphragm 14 is to give a resting/base weight on the diaphragm 14 to give a constant value. The plunger 16 also pushes into the wrist and partially occludes the radial artery. Advantageously, it enables the transmission of the pulsation of the radial artery 20 to be picked up even though the wearer's hand may be at various positions.

There is a layer of gel 18 between the diaphragm 14 and the plunger 16 to filter out interference and sharp changes due to unnatural movement. It also dampens the noise ratio. The plunger depth is specially designed such that in most normal wrists 24, it could occlude not more than half the diameter of the radial artery 20 when the strap is comfortably worn. This will enable full and faithful transmission of the arterial pulsation to be picked up, including the expansion of the arterial walls, the turbulence of the flow and the vibration transmitted along the artery wall from the heart.

Figure 3:
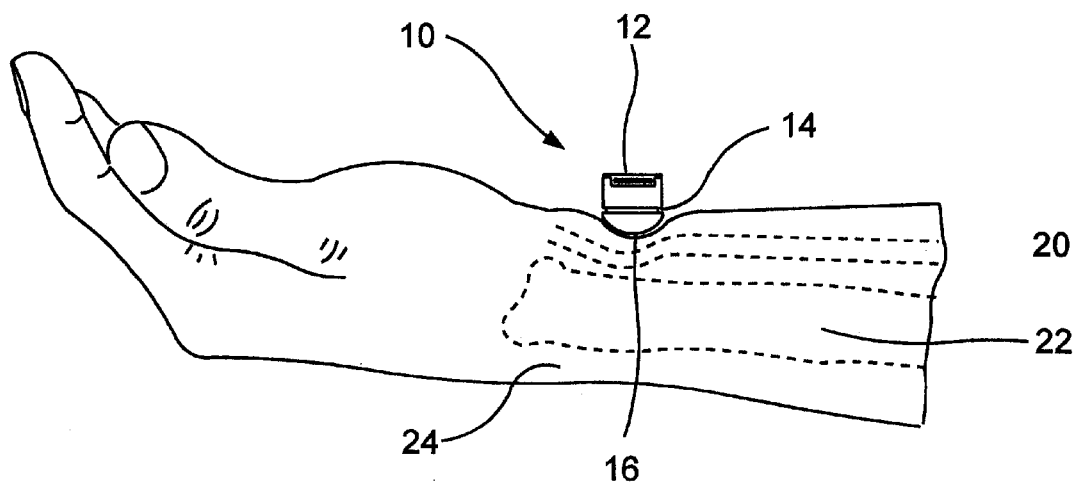
FIG. 3 is a side view of a sensor of FIG. 2 used on the wrist of a wearer and placed adjacent to and partially occluding the radial artery of the wearer.
Figure 4:
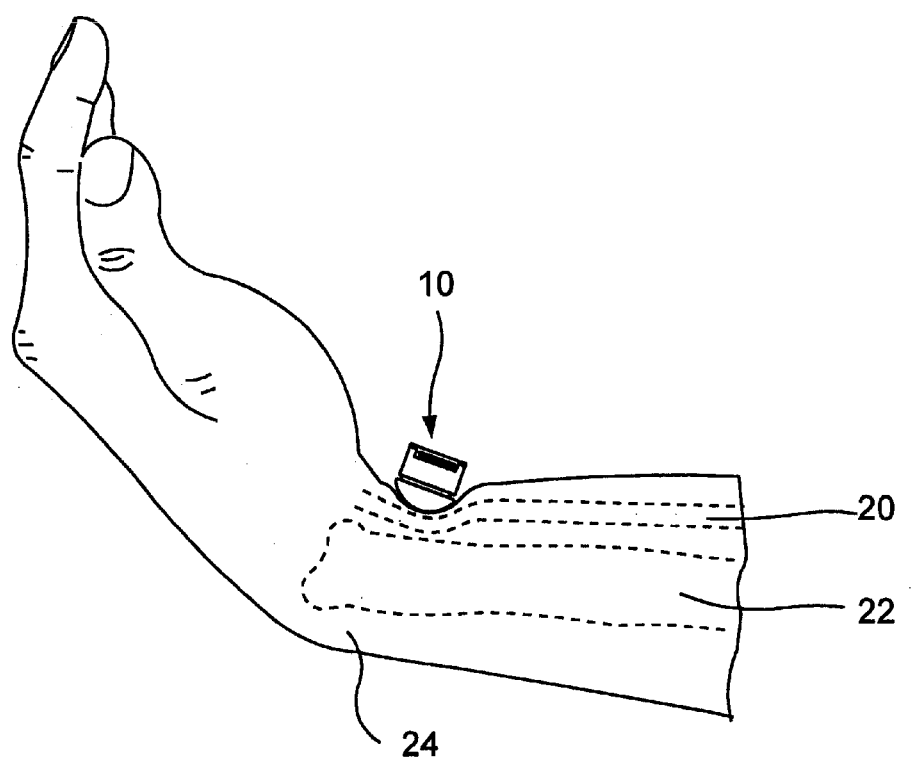
FIG. 4 is an illustration of the sensor placed next to the radial artery wherein the user's hand is flexed.

FIG. 3 is a side view of the sensor 10 of FIG. 2 used on the wrist 24 of a wearer and placed adjacent to and partially occluding the radial artery 20 of the wearer. FIG. 4 is an illustration of the sensor 10 placed next to the radial artery wherein the user's hand is flexed.

The illustration shows that the sensor 10 is preferably placed adjacent to the radial artery 20. The radial artery 20 at the wrist 24 has been chosen because firstly, it rests on the radial bone 22 dorsally. The radial bone 22 allows for full transmission of the pulsation to be felt as it is rigid and would not allow for any significant soft tissue compensation. Vertically, the sensor system 10 is locked in together with the watch straps and watch head as one immovable and unstretchable unit. The plunger 16 is thus behaving similarly to the intra-arterial cannular 2, and the fluid column 3. As the plunger 16 and the diaphragm 14 are the only moving units at each pulsation, the arterial pressure is accurately picked up as a waveform as each heart beat reaches the radial artery. Nevertheless, the advantage is that there is no need for the system to be invasive and it is portable.

The following reasons improve the functionality of the sensor system:

1. For a change in pressure between 0 mmHg–300 mmHg, the displacement of the diaphragm against the pressure variation forms a linear relationship. The range of voltage change in the sensor for such an equation is between 0.5V to 4V, after amplification of the signal.
2. The hemispherical plunger 16 allows for faithful transmission in various wrist positions.
3. The system does not require any fixation of strap pressure. Its main aim is to pick up the waveform of the pressure in the artery for calibration and calculation of blood pressure values in the software program.

The Strap System

Figure 5:
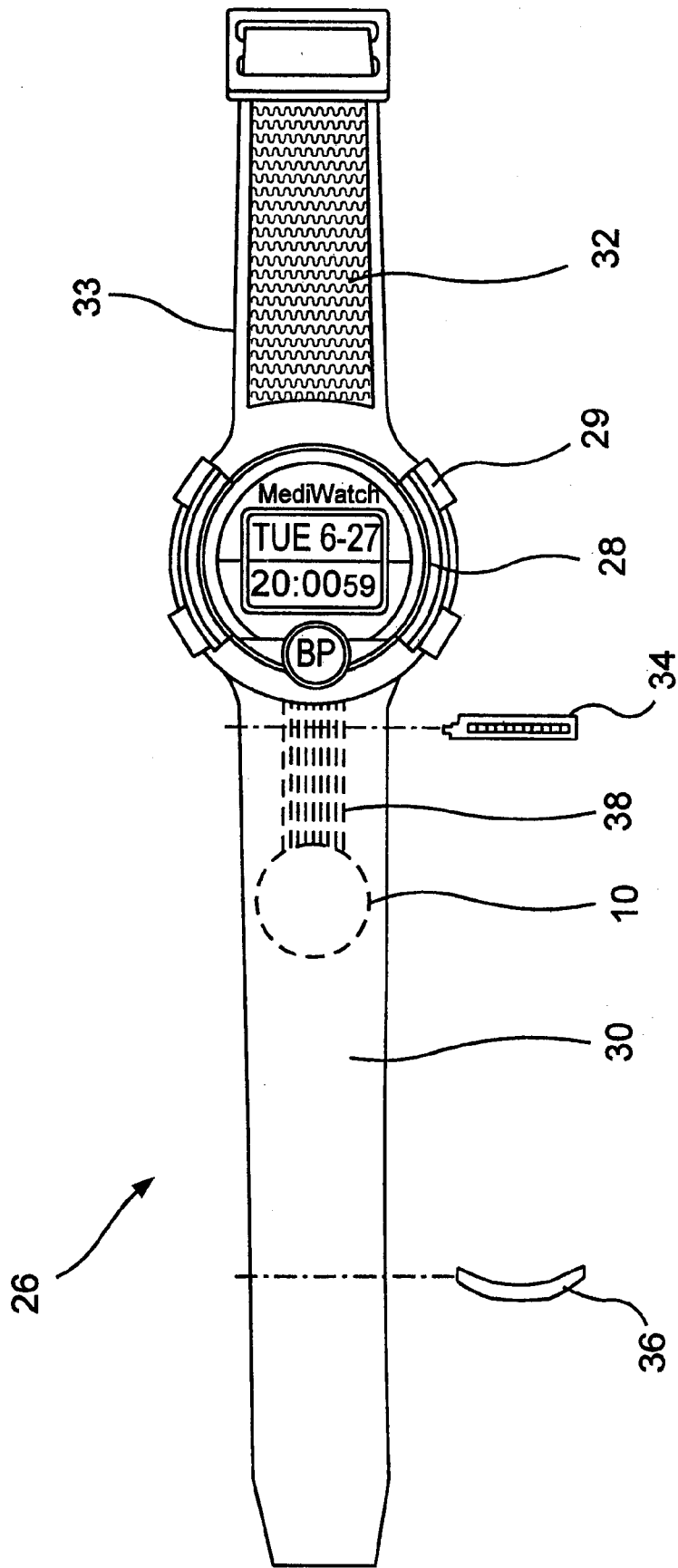
FIG. 5 is a perspective view of a portable blood pressure monitoring device of the present invention as preferably embodied in a watch, that also shows the position of the sensor and the curved strap in cross-section.

FIG. 5 is a perspective view of a portable blood pressure monitoring device of the present invention as preferably embodied in a watch, that also shows the position of the sensor and the curved strap in cross-section.

The watch 26 comprises a watch head/face 28 and buttons 29 to adjust the settings on a liquid-crystal display. There are 2 watch straps, conveniently referred to as the radial strap 30 and the ulnar strap 32 respectively. The sensor 10 is preferably located on the radial strap 30. Between the watch head 28 and the sensor, the radial strap 30 has a generally flat surface 34. After the position of the sensor 10 on the radial strap 30, the radial strap 30 has a generally curved surface 36.

Figure 6:
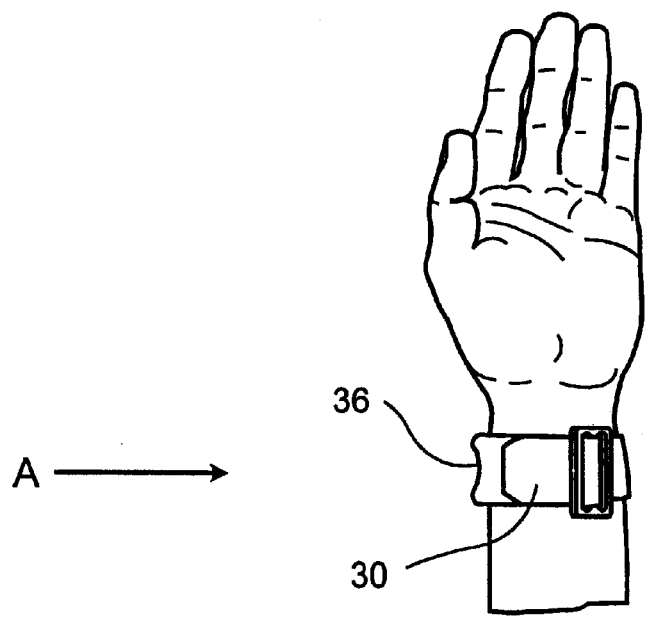
FIG. 6 is an illustration of a hand on which the blood pressure monitoring device is worn, showing that part of the watch strap is curved.
Figure 7:
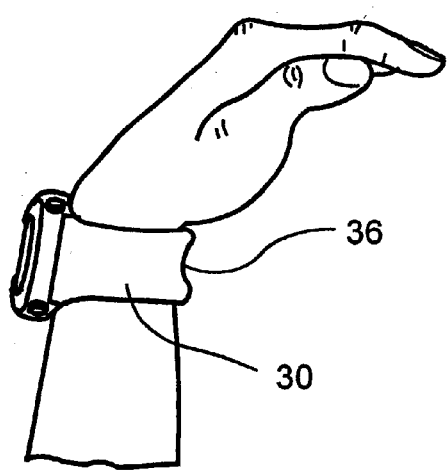
FIG. 7 is a view of the hand of FIG. 6 looking from direction A of FIG. 6.

FIG. 6 is an illustration of a hand on which the blood pressure monitoring device is worn, showing that part of the radial strap 30 is curved. FIG. 7 is a view of the hand of FIG. 6 looking from direction A of FIG. 6.

Consideration has to be made for flexion and extension of the wrist 24. The main movement that affects the pressure change in the strap 30,32 and/or sensor 10 abutting the artery is flexion, i.e. the forward bending of the wrist 24. It is primarily this movement that the stiff, rigid straps of the prior art do not compensate for. The change in the pressure of the strap 30,32 when the strap circumference is fixed can be great. The movement may even disengage the sensor 10 from the skin temporarily. To allow for this flexion, an additional feature has been designed in the strap of both the ulnar strap 32 and radial strap 30. This is to make them slightly concave at both straps, approximately 3 cm from the watch head. (see FIGS. 5, 6 and 7) With this feature, the change in position due to the flexion or extension of the wrist 24 is well compensated for enabling the positions of the watch 26 or sensor 10 to be still kept relatively constant.

The change in voltage as picked up by the piezo-resistance die of the sensor 10 is transmitted into the watch head 28 via 4 cables 38 concealed between 2 layers of the radial strap 30, made of polyurethane resin material. These cables are laid during the injection moulding of the radial strap 30.

In order to keep the sensor system fixed in position over the radial artery despite a moving wrist, the inventors have devised a 3-point fixation system.

Figure 8:
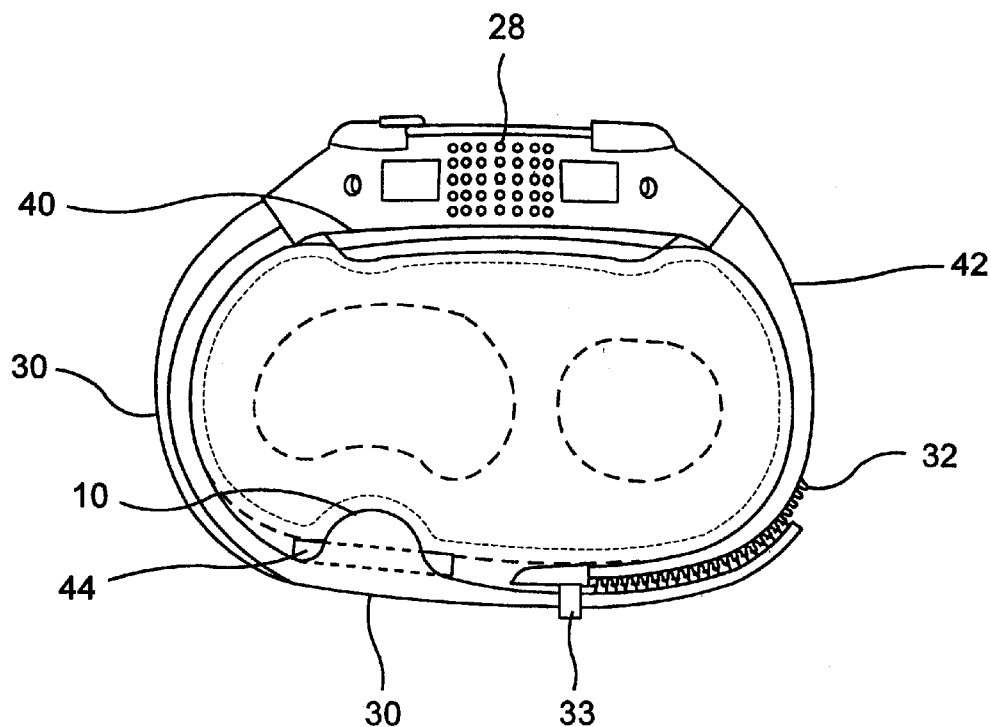
FIG. 8 is a side view of the watch head demonstrating the 3-point anchoring principle of the watch, including anchor-points at the undersurface of the watch head, the radial strap and the ulnar strap.

Firstly, the watch head 28 is designed such that the back of the watch head 28 has a curved surface and preferably concave so that it sits snugly on the human wrist. FIG. 8 is a side view of the watch head 28 demonstrating the 3-point anchoring principle of the watch 26, including anchor-points at the undersurface 40 of the watch head 28, the radial strap 30 and the ulnar strap 32. This provides stability, primarily in the position of the watch head 28. A strip of flexible rubber material 42 is located near the circumference of the curved undersurface 40 of the watch 26. A gentle push on the watch head 28 would provide suction pressure to locate the watch head 28 onto the wrist 24 much like that of a rubber suction-cup.

Figure 9:
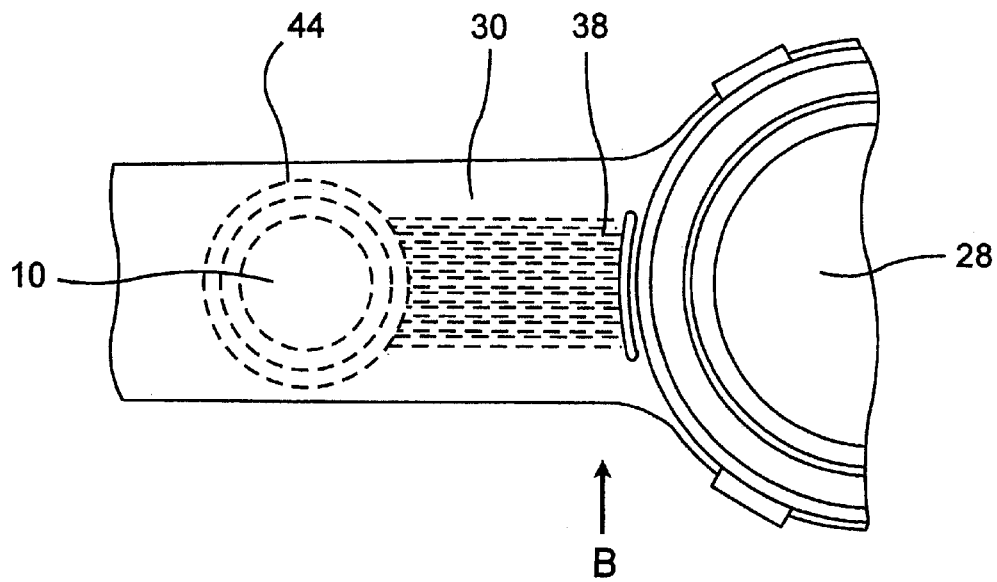
FIG. 9 is a top view of one strap of the watch of the described embodiment illustrating the position of the sensor relative to the watch face.
Figure 10:
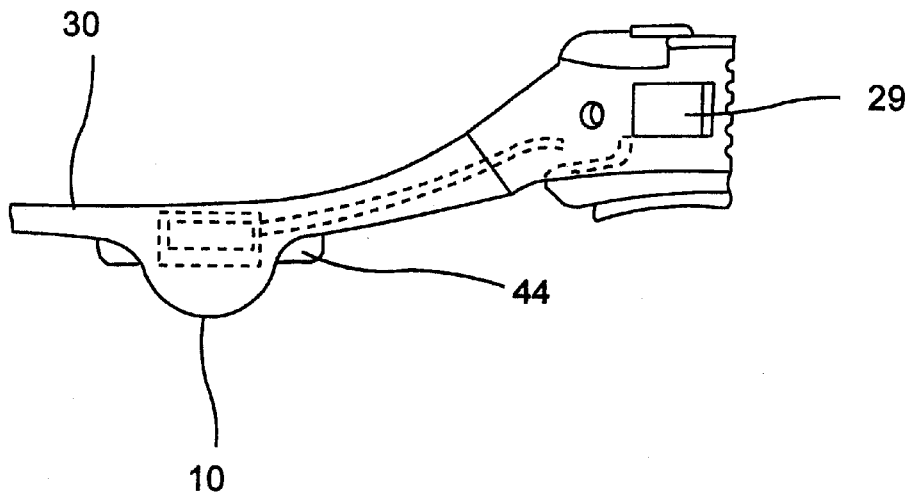
FIG. 10 is a side view of the watch illustrated in FIG. 9 looking from position B in FIG. 9.

Secondly, the straps of the watch consist of a radial strap 30 and an ulnar strap 32, each contributing a point of anchor. FIG. 9 is a top view of the radial strap 30 of the watch 26 of the described embodiment illustrating the position of the sensor 10 relative to the watch head/face 28. Further, FIG. 10 is a side view of the watch 26 illustrated in FIG. 9 looking from position B in FIG. 9.

The radial strap 30 houses the sensor 10 that includes the transducer 12, diaphragm 14, gel 18 and hemispherical plunger 16. The hemispherical protrusion of the plunger 16 is adjacent to the radial artery 20. This position of the plunger 16 adjacent to the radial artery 20 to detect changes of pressure should be kept relatively constant. Thus, a circular band of sticker pad 44 surrounds the plunger 16. Once the radial artery 20 is located, the plunger 16 is placed directly onto the position and a firm but gentle pressure is applied to fix the sensor position.

The ulnar strap 32 is made of a nylon material that is unstretchable and soft, but strong and adheres neatly to the wrist. Its quality is that it does not move easily over the skin. The ulnar strap 32 is tightened last in a comfortable but firm tension. A section of velcro material (illustrated as 33, in FIG. 5) may be used to adhere the radial strap 30 to the ulnar strap 32.

Following from the above description of the preferred embodiment, the steps in adjusting the blood pressure monitoring device would be to:

1. Locate the position of the radial artery 20.
2. Place the sensor 10 directly on the position.
3. Press firmly for sticker pad 44 to hold.
4. Place watch head 28 on dorsum of wrist 24.
5. Press firmly to induce a suction effect.
6. Tighten the velcro strap 33 (on the ulnar strap 32 and radial strap 30) to a comfortable tension.

Data Collection

Figure 11:
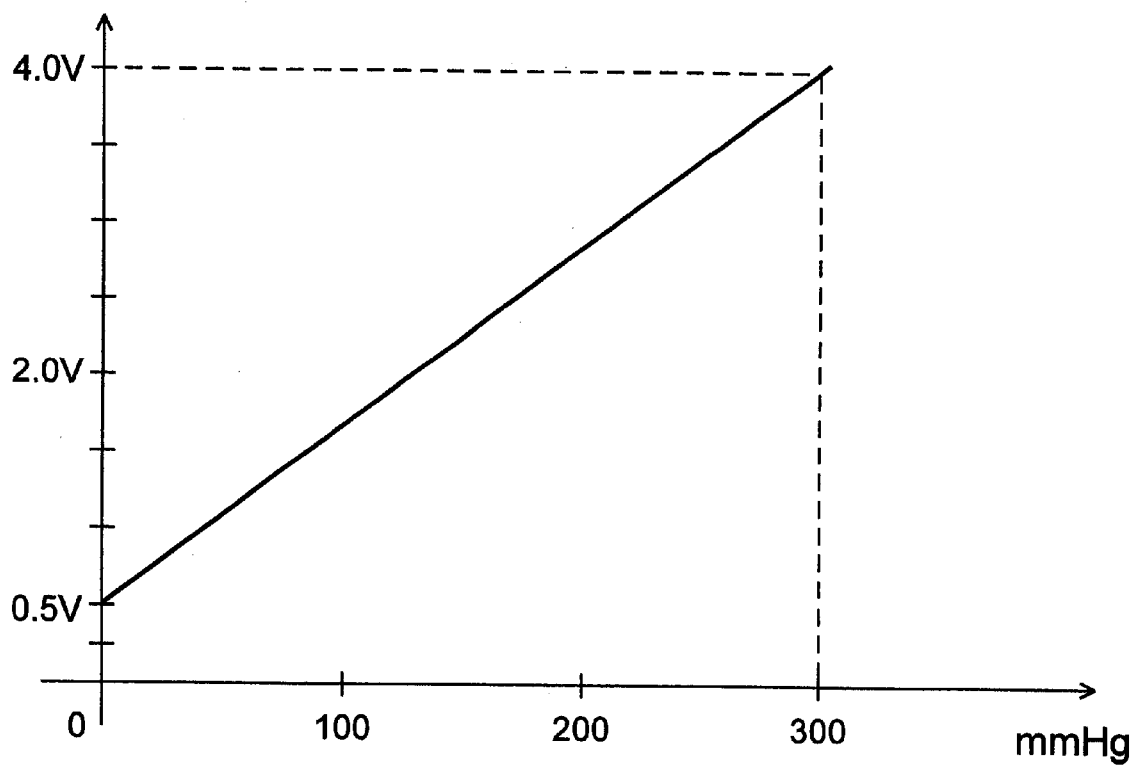
FIG. 11 is a sample graph showing the voltage output produced by the sensor according to the described embodiment in response to a pressure applied to the sensor.

FIG. 11 is a sample graph showing the voltage output produced by the sensor 10 according to the described embodiment in response to a pressure applied to the sensor 10. As mentioned above, the sensor includes a transducer 12. The transducer is preferably one which provides a change in voltage that is directly proportional to the amount of pressure applied onto the transducer to produce a linear graph similar to the one illustrated in FIG. 11. It was found that a suitable transducer is the Foxboro/ICT Model 1865 transducer.

With the sensor system 10 used, and a microprocessor employed in the watch head 28 to calculate the readings produced by the sensor 10, up to 19 values per second were obtained during tests on the device. By varying the intervals of each detection, i.e. the number of values per second, the inventors have been able to obtain optimal waveforms at 10 readings per second. These waveforms correspond to the systolic/diastolic cycle of the heart when the readings were compared simultaneously with conventional Doppler machines.

Figure 12:
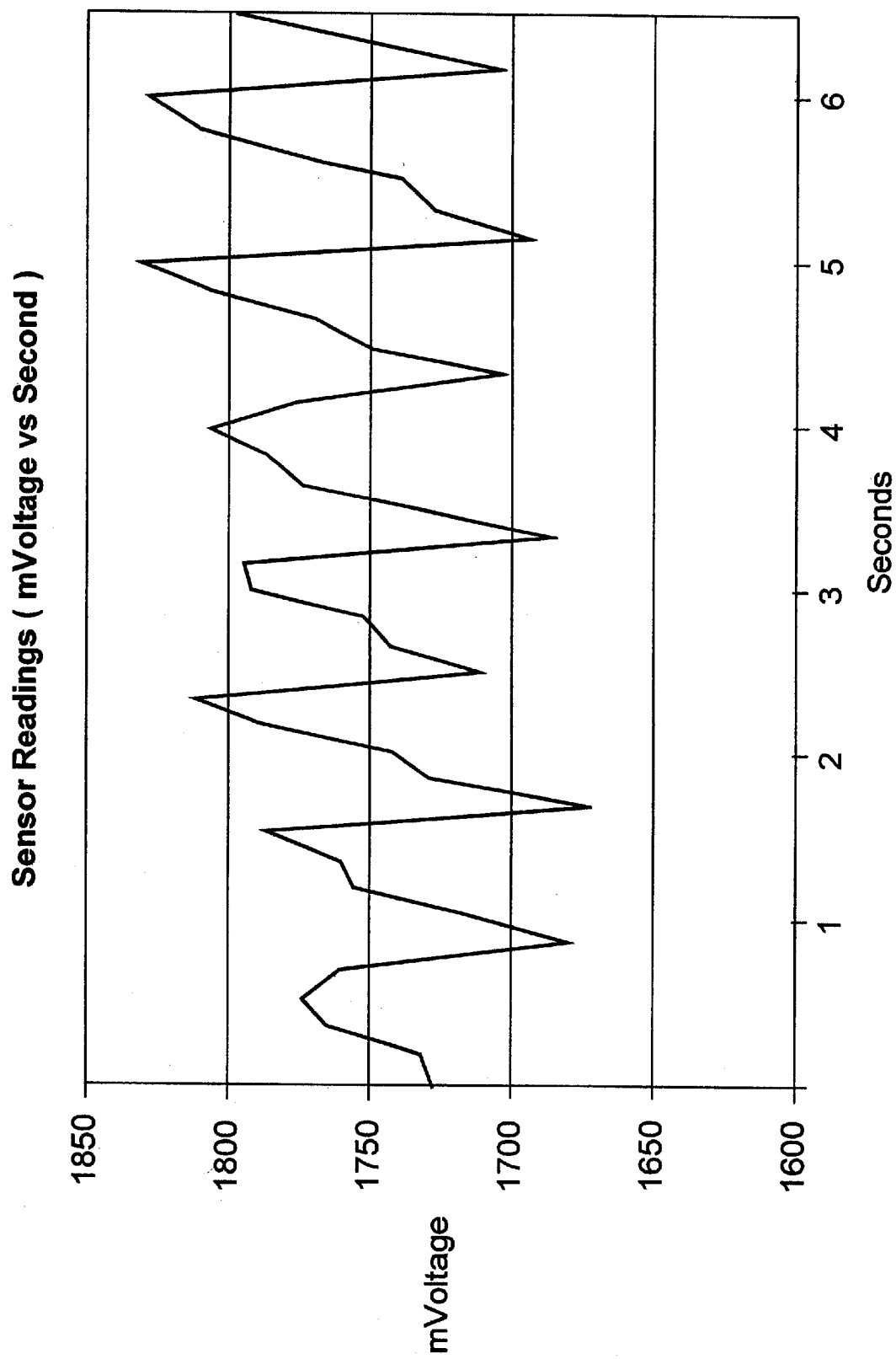
FIG. 12 is a sample chart showing sensor readings of a wearer's blood pressure taken over 6 seconds.

FIG. 12 is a sample chart showing sensor readings of a wearer's blood pressure taken over 6 seconds. There are a total of 6 systolic and 6 diastolic values provided. These systolic and diastolic readings are averaged under the calibration procedure described below.

Calibration

Figure 13:
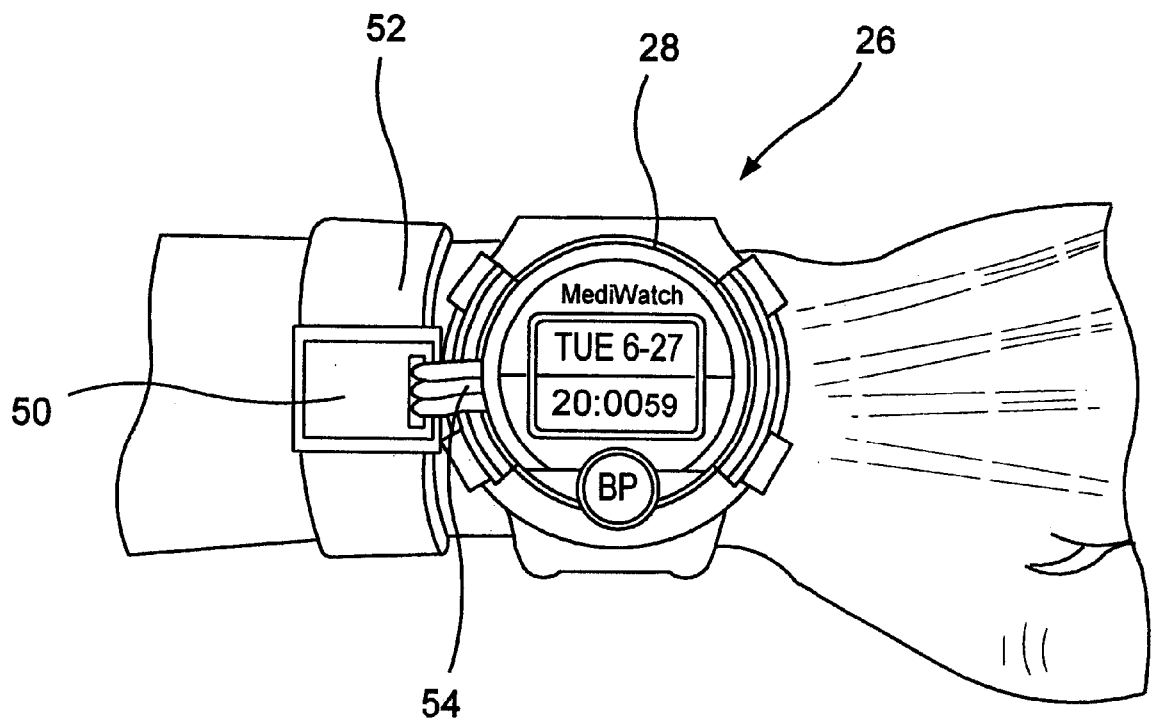
FIG. 13 is a perspective view of an auto-calibrator that is connected to the blood pressure monitoring device for calibration purposes.

FIG. 13 is a perspective view of an auto-calibrator 50 that is connected to the blood pressure monitoring device (watch 26) for calibration purposes.

The auto-calibrator 50 has been designed to give an absolute value of the blood pressure using a conventional occlusive method. The concept is that a separate wrist-band 52 is strapped to the wrist 24 next to the watch 26. The wrist-band 52 uses a cuff system that is automated, self-inflating and measures the absolute blood pressure for reference by the blood pressure monitoring device (watch 26).

Instead of a liquid crystal display on the said auto-calibrator 50, the data read by the wrist-band may be immediately processed by its microprocessor (not shown) and downloaded to the watch 26 via a 3-pin outlet 54 to calibrate the system.

The electronically operated cuff-type non-continuous blood-pressure monitor set at the wrist level is already available in the market. The inventors have designed a software program and a microprocessor to download the systolic and diastolic readings into the watch-head 28 itself. Simultaneous with the calibrator 50 taking the systolic and diastolic reading, the sensor 10 of the watch 26 takes the blood pressure readings and waveforms of the last 6 seconds. As mentioned, 10 readings are taken per second and 60 readings are therefore taken during the 6 seconds. A sample wave-form has been illustrated in FIG. 12. The average of the peak readings (systolic) are calculated after sampling to obtain greater accuracy. Sampling includes filtering readings that do not correspond to an expected wave-form (for example, muscle contractions produce a sharper and symmetrically-formed peak). Correspondingly, the average of the trough readings (diastolic) are also calculated. The values of the average systolic and diastolic readings respectively are compared to the systolic and diastolic readings from the auto-calibrator 50, to assign absolute values to the sensor readings with reference to a voltage level. It is then verified by the software program using the linear relationship of the pressure against voltage change characterized by the sensor 10 (a chart illustrating the linear relationship is shown in FIG. 11) as a guide.

The calibrator 50 can then be removed and continuous blood pressure monitoring commences. At any one time, the value of the blood pressure can be checked or verified by the calibrator 50 (which reading may be displayed on the watch-head 28). This is useful when the alarm is sounded when, for example, the blood pressure is outside a pre-determined range, or reaches a preset value.

The pulse rate may also be calculated simply by the time interval between 2 systolic or diastolic values divided by 60 seconds. Therefore, this gives a beat-to-beat heart rate and therefore allows verification of the regularity of the heart beat when the data is provided over a period of time.

Steps in Calibration

FIG. 14 is a flow-chart summarizing the steps involved in the calibration procedure. In brief, these are to:

1. Put on the auto-calibrator adjacent to the watch in a neutral position of the wrist.
2. Connect the calibrator to the watch through the physical interface.
3. Switch on the calibrator to inflate and deflate the cuff automatically, thereby obtaining the systolic and diastolic readings. These readings are displayed on the watch-head and absolute values are assigned to the sensor readings.
4. Remove the auto-calibrator when calibration is complete.

Collection and Storage of Data

Figure 15:
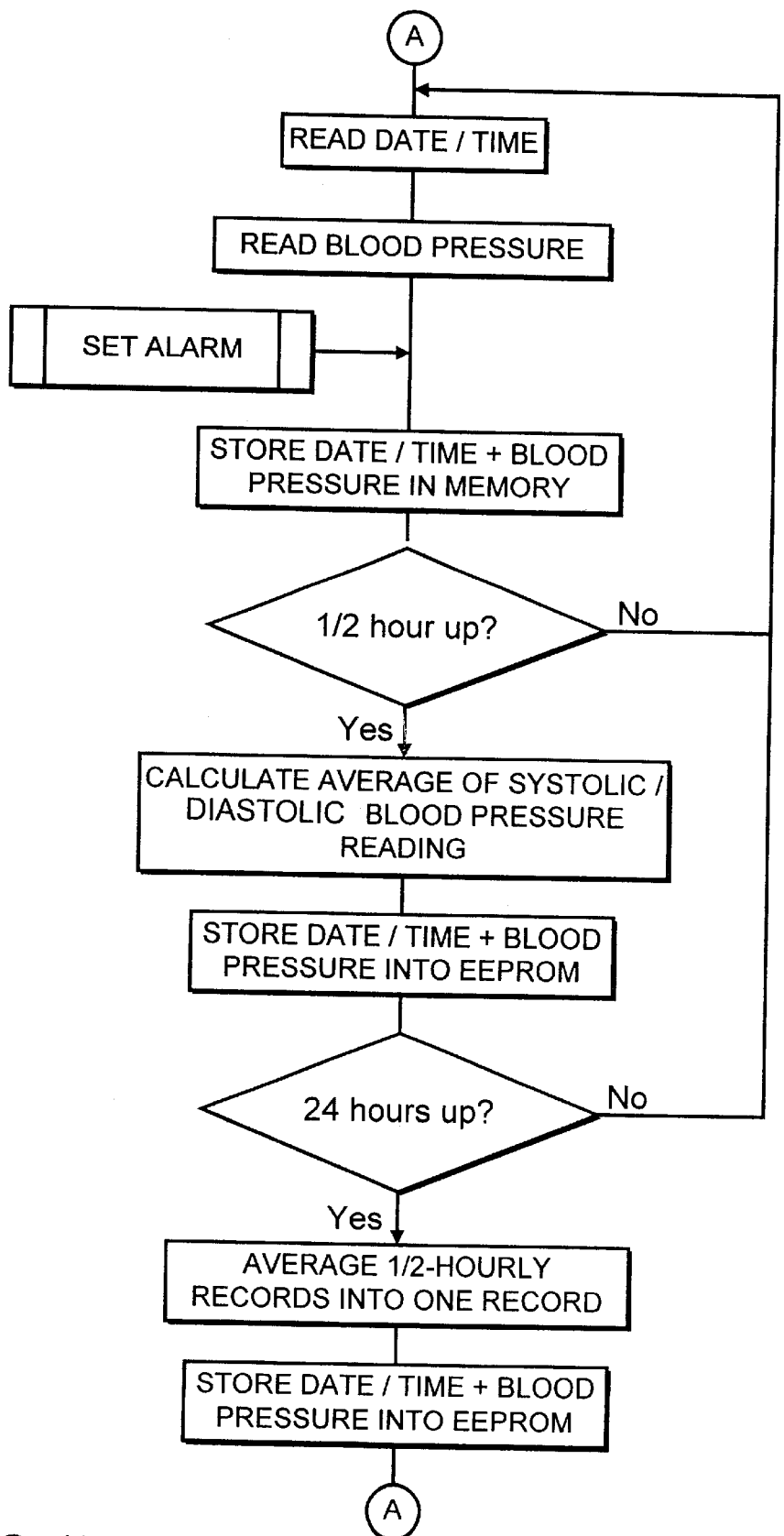
FIG. 15 is a flow-chart summarizing the steps involved in taking blood pressure readings.

The main objective of the collection and storage of data is to be able to see the trend and determine the danger-point of the change in blood pressure during a pre-determined period of time. Data can be printed or otherwise downloaded to a storage device for such period. Since blood pressure readings are stored in the watch memory module with respect to a time, such trends in change of blood pressure over a period of time can be monitored. FIG. 15 is a flow-chart summarizing the steps involved in taking blood pressure readings.

Communication Tool

Figure 16:
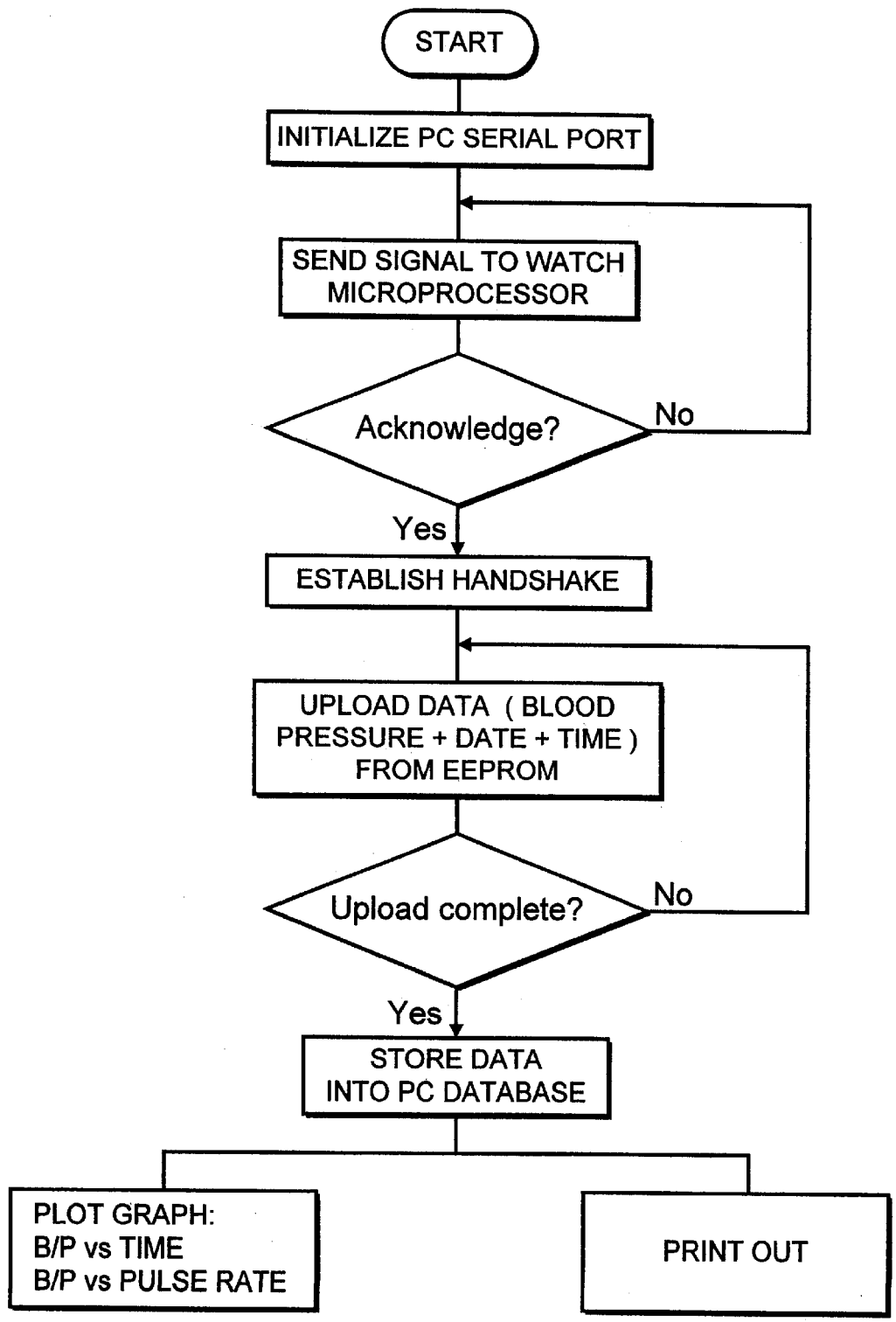
FIG. 16 is a flow-chart summarizing the steps involved in the data transfer and communications aspect of the invention.

The watch can further be connected to a personal computer to download data or to a printer to print data. FIG. 16 is a flow-chart summarizing the steps involved in the data transfer and communications aspect of the invention. Although the watch may be connected directly to a personal computer by a direct cable connection such as RS 323, Universal Serial Bus or other similar interface, it is contemplated that the watch could be connected to bluetooth device for wireless connection.

Setting of Alarm

Figure 17:
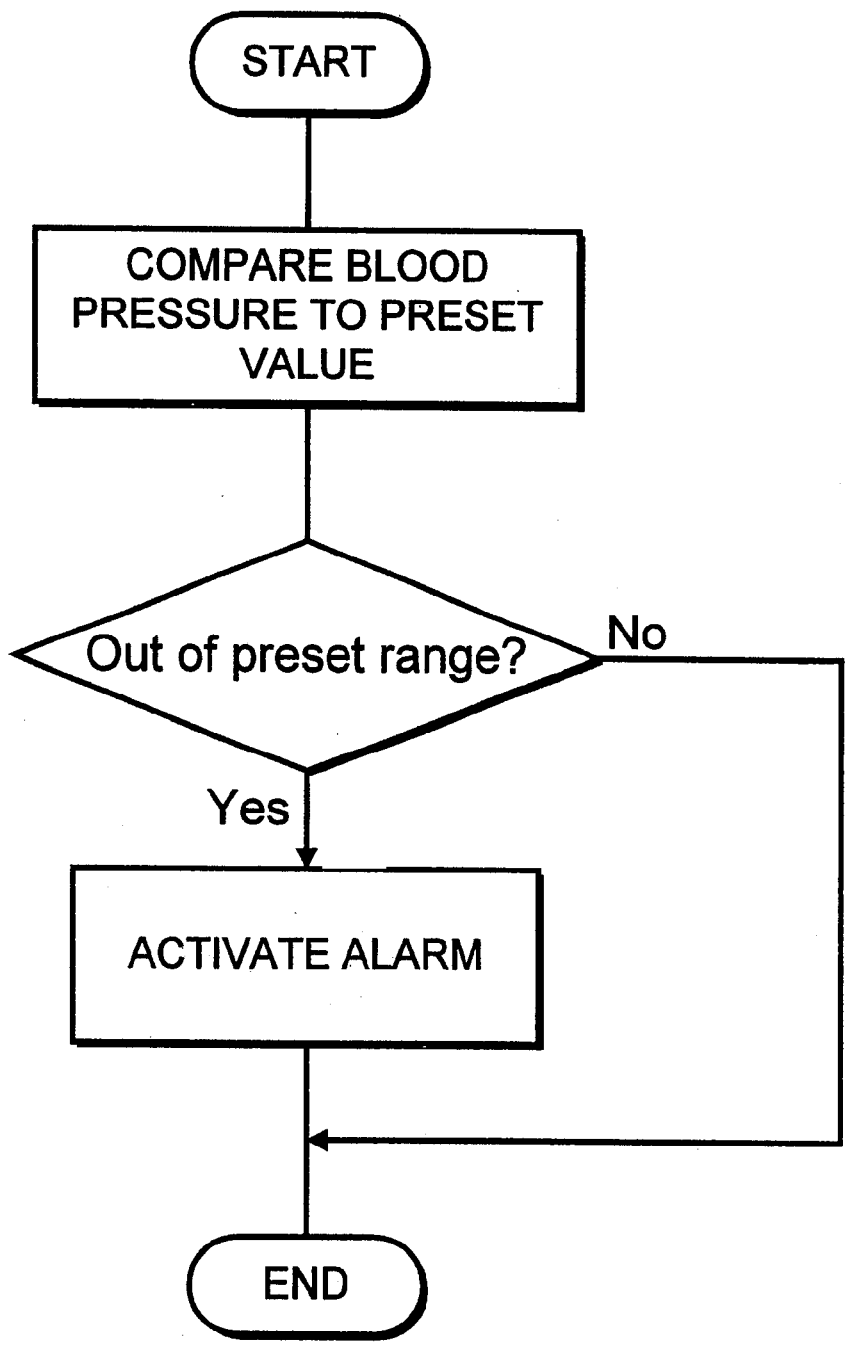
FIG. 17 is a flow-chart summarizing the steps involved in the watch determining whether to sound an alarm to warn of potentially dangerous blood pressure levels.

It is believed that many catastrophic events occur when the blood pressure suddenly increases or decreases drastically in a patient. This is true in some stroke patients and very evident in pre-eclampsia patients. The aim of the continuous monitoring is firstly to discover and help the control of blood pressure. Secondly, in some cases, a tragedy may be avoided if there is an alarm system to detect these sudden and drastic changes. The alarm can be preset at the factory or individually set, and multiple alarms can be set for the blood pressure or pulse rates. FIG. 17 is a flow-chart summarizing the steps involved in setting the alarm in the watch to warn of potentially dangerous blood pressure levels.

Figure 18:
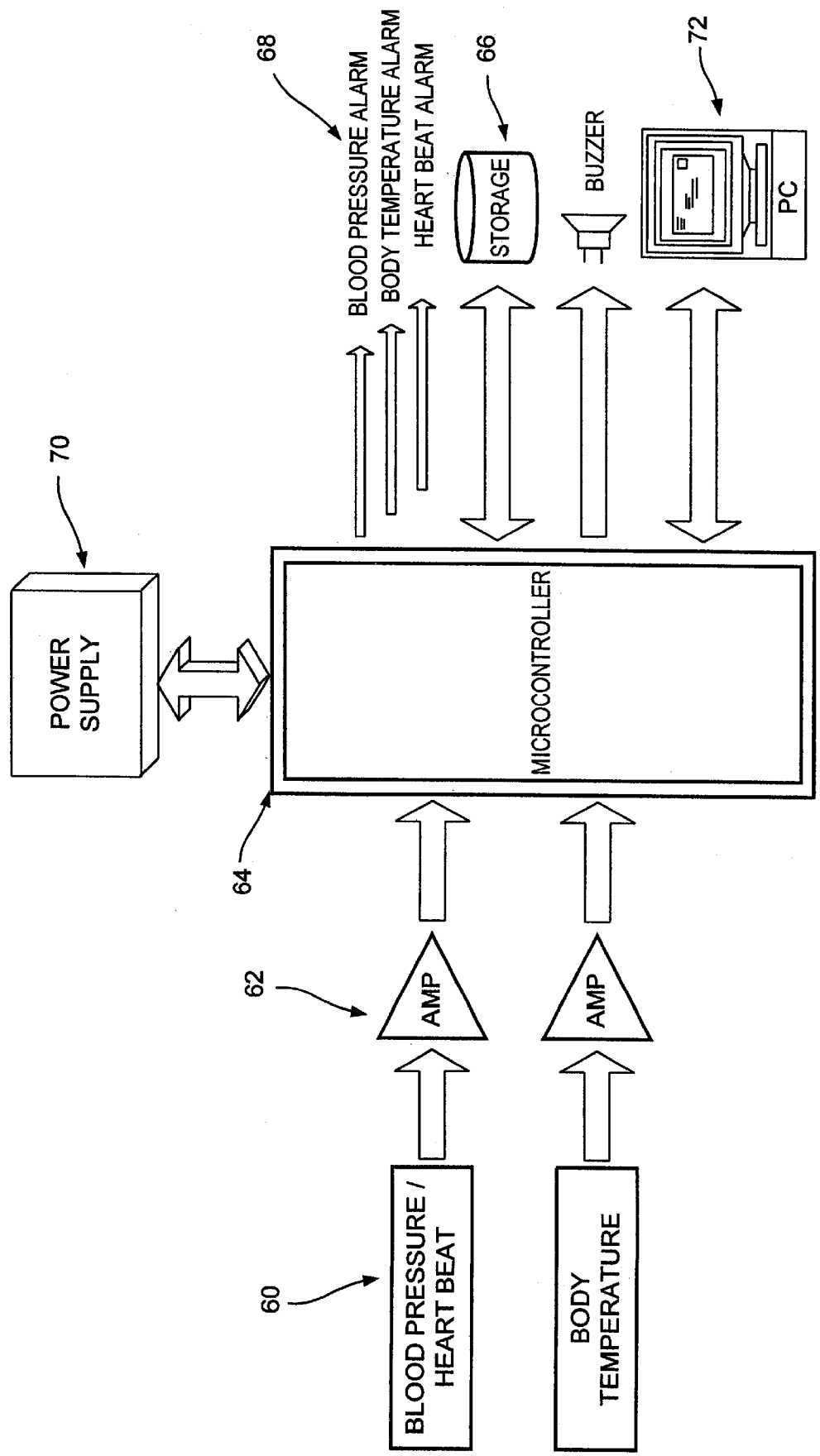
FIG. 18 is a schematic block diagram of a blood pressure monitoring device designed according to the preferred embodiment of the present invention.

FIG. 18 is a schematic block diagram of a blood pressure monitoring device designed according to the preferred embodiment of the present invention. Blood pressure readings 60 are taken by the sensor 10 and are amplified by amplifier 62 to a value that can be read by a microcontroller/microprocessor 64. An example of the microcontroller/microprocessor 64 suitable for use with the device may be the Motorola 68 series of microprocessor. Optionally, a temperature sensor as found in the art could also be included into the device to read the body temperature, and send the readings to the microcontroller/microprocessor 64. The readings are preferably stored into a storage component 66, as previously mentioned. The microcontroller/microprocessor 64 may also be coupled to various alarms 68, such as blood pressure, body temperature and heart-beat alarms to warn the user if a pre-determined value is reached. The device is powered by a power supply 70. The readings, whether taken in real-time or stored in the storage component 66, can be downloaded into a personal computer 72 or other communication device.

Figure 19:
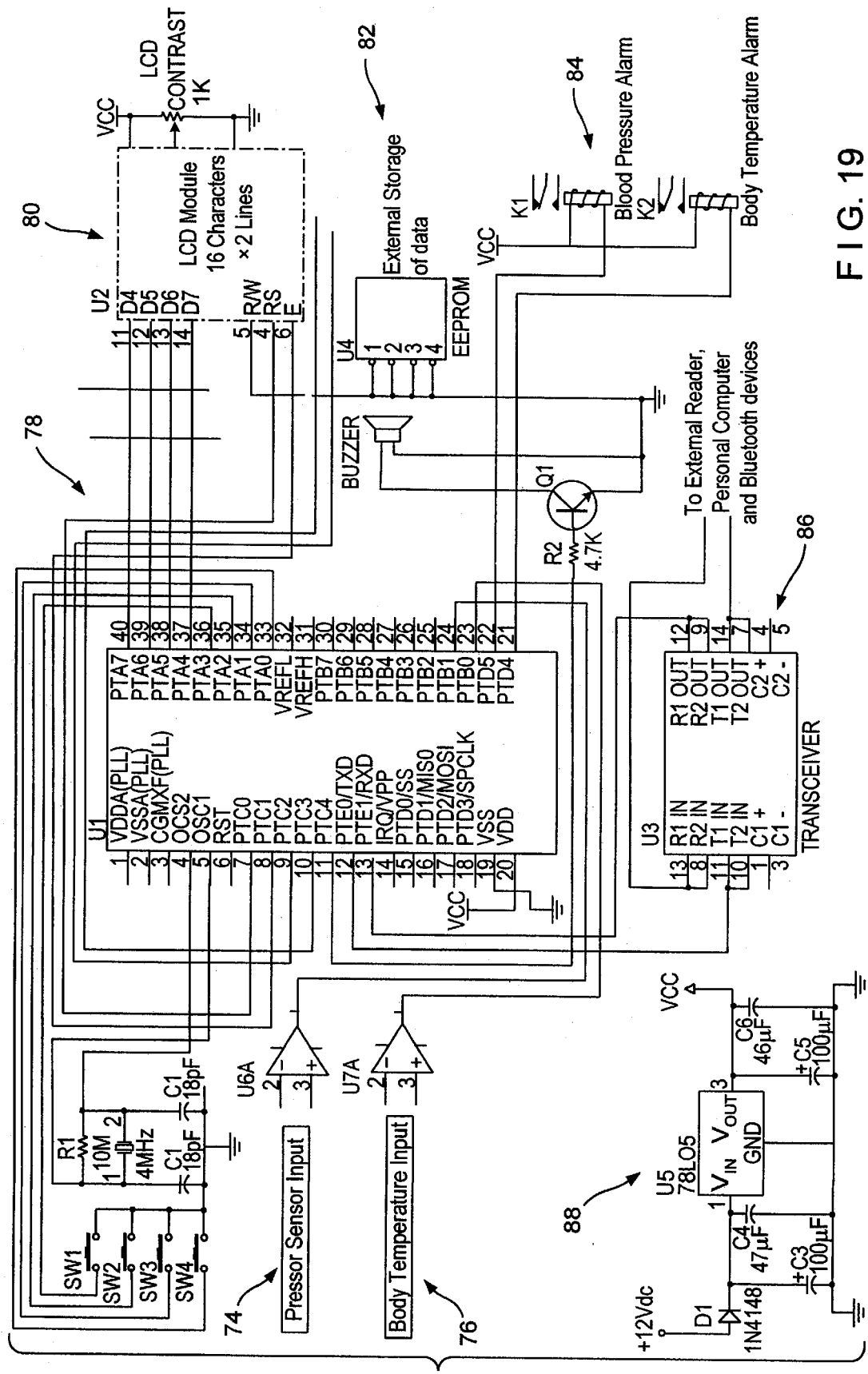
FIG. 19 is a schematic circuit diagram of a blood pressure monitor device designed according to the preferred embodiment shown in FIG. 18.

FIG. 19 is a schematic circuit diagram of a blood pressure monitor device designed according to the preferred embodiment shown in FIG. 18. It demonstrates the circuit connection of the primary components of the device, including the pressure sensor input 74, body temperature input 76, microprocessor 78, liquid-crystal display module 80 for display on the device, the EEPROM storage 82, blood pressure alarm 84, transceiver 86 and power supply 88.

While a particular embodiment of the invention has been shown and described, it will be obvious to those skilled in the art that changes and modifications of the present invention may be made without departing from the invention in its broader aspects. As such, the scope of the invention should not be limited by the particular embodiment and specific construction described herein but should be defined by the appended claims and equivalents thereof. Accordingly, the aim in the appended claims is to cover all such changes and modifications as fall within the spirit and scope of the invention.

What is claimed is:

1. A device for continuously monitoring a user's arterial blood pressure, comprising:

sensor means adapted to continuously detect said blood pressure and to generate signals representative thereof by contact with an external surface of the user's body at a location adjacent an artery;

a strap for surrounding a limb or some other part of the user's body, to securely hold the sensor means in operable contact with the user's body, at least a portion of the strap having an inner surface configured in cross section to curve inwardly towards the user's body; and microprocessor means for interpreting said signals generated by the sensor means to determine actual arterial blood pressure;

wherein the sensor means includes a projecting portion for detecting and transmitting changes in blood pressure, and wherein the projecting portion is adapted to effect at least partial occlusion of the artery at the location.

2. The device is claimed in claim 1 wherein said strap is adapted to non penetratingly press the projection portion into the surface of the user's body for operable contact therewith at said location adjacent the artery.

3. The device as claimed in claim 1 wherein the sensor means includes a transducer and wherein the projecting portion of the sensor means is adapted to transmit detected changes in blood pressure to the transducer.

4. The device as claimed in claim 3 wherein the projecting portion of the sensor means is a dome-shaped plunger connected to the transducer.

5. The device as claimed in claim 4 including at least one stabilising pad for inhibiting movement of the sensor means relative to the user's body.

6. The device as claimed in claim 3 including at least one stabilising pad for inhibiting movement of the sensor means relative to the user's body.

7. The device as claimed in claim 2 wherein the sensor means includes a transducer and wherein the projecting portion of the sensor means is adapted to transmit detected changes in blood pressure to the transducer.

8. The device as claimed in claim 7 wherein the projection portion of the sensor means is a dome-shaped plunger connected to the transducer.

9. The device as claimed in claim 8 wherein the plunger is hemispherical.

10. The device as claimed in claim 2 including at least one stabilising pad for inhibiting movement of the sensor means relative to the user's body.

11. The device as claimed in claim 4 wherein the plunger is hemispherical.

12. The device as claimed in claim 1 including at least one stabilising pad for inhibiting movement of the sensor means relative to the user's body.

13. The device as claimed in claim 12 wherein one said stabilising pad is positioned adjacent the sensor means and includes adhesive properties for adherence to the user's body.

14. The device as claimed in claim 1 wherein the sensor means is mounted on the strap.

15. The device as claimed in claim 14 further including a casing for housing the microprocessor means and incorporating a display panel for displaying to the user the monitored values of the user's blood pressure, wherein the microprocessor means and the sensor means are in electrical connection, and wherein the casing is also adapted to be secured to the use by the strap at a position spaced apart from the sensor means.

16. The device as claimed 15 wherein said device is adapted to be worn at the patient's wrist with the sensor means positioned adjacent he radial artery.

17. The device as claimed in claim 16 wherein the casing and display panel also function as a wrist-watch.

18. The device as claimed in claim 1 further including a casing for housing the microprocessor means and incorporating a display panel for displaying to the user the monitored values of the user's blood pressure, wherein the microprocessor means and the sensor means are in electrical connection, and wherein the casing is also adapted to be secured to the user by the strap at a position spaced apart from the sensor means.

19. The device as claimed in claim 18 wherein said device is adapted to be worn at the patient's wrist with the sensor means positioned adjacent the radial artery.

20. The device as claimed in claim 19 wherein the casing and display panel also function as a wrist-watch.

21. The device as claimed in claim 8 including at least one stabilising pad for inhibiting movement of the sensor means relative to the user's body.

22. A device for continuously monitoring a user's arterial blood pressure, including:

sensor means adapted to continuously detect said blood pressure and to generate signals representative thereof by contact with an external surface of the user's body at a location adjacent an artery;

attachment means for securely holding the sensor means in operable contact with the user's body at the said location, said attachment means including a strap for surrounding a limb or some other part of the user's body, said strap adapted to securely hold the sensor means in operable contact with the patient, at least a portion of the strap having a concavely curved cross section, the strap cross section configured to curve inwardly towards the user's body; and microprocessor means for interpreting said signals generated by the sensor means to determine actual arterial blood pressure;

wherein the sensor means includes a projecting portion for detecting and transmitting changes in blood pressure, and wherein the projecting portion is adapted to effect at least partial occlusion of the artery at the said location.

23. The device as claimed in claim 22 including at least one stabilising pad for inhibiting movement of the sensor means relative to the user's body.

24. The device as claimed in claim 23 wherein one said stabilising pad is positioned adjacent the sensor means and includes adhesive properties for adherence to the user's body.

* * * * *

UNITED STATES PATENT AND TRADEMARK OFFICE
CERTIFICATE OF CORRECTION

PATENT NO. : 6,443,906 B1
DATED : September 2, 2002
INVENTOR(S) : Choon Meng Ting et al.

It is certified that error appears in the above-identified patent and that said Letters Patent is hereby corrected as shown below:

Column 12,
Line 8, "8" should read -- 18 --.

Signed and Sealed this

Seventeenth Day of August, 2004

JON W. DUDAS
*Acting Director of the United States Patent and Trademark Office*